US012635677B2

(12) United States Patent
Harlacher et al.

(10) Patent No.: US 12,635,677 B2
(45) Date of Patent: May 26, 2026

(54) ATTRACTANT POD CLIP

(71) Applicant: Woodstream Corporation, Lancaster, PA (US)

(72) Inventors: Drew Harlacher, Delta, PA (US); Luke Haney, Lititz, PA (US)

(73) Assignee: Woodstream Corporation, Lancaster, PA (US)

( * ) Notice: Subject to any disclaimer, the term of this patent is extended or adjusted under 35 U.S.C. 154(b) by 20 days.

(21) Appl. No.: 18/436,486

(22) Filed: Feb. 8, 2024

(65) Prior Publication Data

US 2025/0255287 A1 Aug. 14, 2025

(51) Int. Cl.
*A01M 1/02* (2006.01)

(52) U.S. Cl.
CPC ............ *A01M 1/02* (2013.01); *A61L 2209/15* (2013.01)

(58) Field of Classification Search
CPC .......... A01M 1/02; A01M 1/10; A01M 1/103; A01M 1/106; A61L 2209/15
USPC ........ 220/500; 43/122, 123, 131, 132.1, 133
See application file for complete search history.

(56) References Cited

U.S. PATENT DOCUMENTS

| | | | | | |
|---|---|---|---|---|---|
| 5,932,147 | A | * | 8/1999 | Chen | B60H 3/0007 261/DIG. 65 |
| 6,102,660 | A | * | 8/2000 | Lee | A61L 9/122 454/157 |
| 6,807,768 | B2 | * | 10/2004 | Johnson | A01M 25/004 43/131 |
| 10,178,861 | B2 | * | 1/2019 | Leier | A01M 1/02 |
| 2005/0127538 | A1 | * | 6/2005 | Fabrega | A01M 1/2033 261/104 |
| 2008/0072474 | A1 | * | 3/2008 | Chen | A01M 1/02 43/107 |
| 2011/0038761 | A1 | * | 2/2011 | Saleh | A61L 9/122 422/124 |
| 2013/0266486 | A1 | * | 10/2013 | Wu | A61L 9/12 422/123 |
| 2014/0145005 | A1 | * | 5/2014 | Westphal | A61L 9/12 239/59 |
| 2014/0237892 | A1 | * | 8/2014 | Peden | A01M 1/20 43/109 |
| 2014/0311015 | A1 | * | 10/2014 | Oehlschlager | A01M 1/023 43/107 |
| 2015/0217017 | A1 | * | 8/2015 | Venisti | B60H 3/0028 239/55 |
| 2016/0051717 | A1 | * | 2/2016 | Esses | A61L 9/00 454/337 |
| 2018/0288992 | A1 | * | 10/2018 | Gallegos | A01M 1/106 |
| 2021/0368765 | A1 | * | 12/2021 | Feo | A01M 1/10 |
| 2022/0132824 | A1 | * | 5/2022 | Toledo | A01M 1/145 43/113 |
| 2022/0161635 | A1 | * | 5/2022 | Reshetnyak | A61L 9/12 |
| 2023/0123062 | A1 | * | 4/2023 | Lubic | A01M 1/14 43/107 |

FOREIGN PATENT DOCUMENTS

WO WO-2020058245 A1 * 3/2020 .......... A01M 1/2055

* cited by examiner

*Primary Examiner* — Rafael A Ortiz
(74) *Attorney, Agent, or Firm* — Barley Snyder

(57) ABSTRACT

An insect bait device includes a cover. The insect bait device further includes a bait vessel. The insect bait device further includes a mount device, the mount device includes a pair of resilient hooks.

13 Claims, 6 Drawing Sheets

24

22

74

76

ATTRACTANT POD CLIP

FIELD OF THE INVENTION

The present invention pertains to attractant pods and, more particularly, to an improved method of attaching attractant pods to various types of insect traps.

BACKGROUND

A variety of flying insect pest traps containing an attracting agent that are used to control flying insect pests such as small flies, etc., are available on the market. The flying insect pest trap is required to have a characteristic structure as well as an attracting agent having a high attracting effect in order to efficiently attract flying insect pests into the trap. These insect traps often utilize replaceable attractant pods containing substances such as pheromones or baits to lure insects effectively to the trap. However, existing attractant pods have limitations in their attachment mechanisms, leading to difficulties for users in securely affixing the pods to different types of traps. The need for an updated attachment method that offers versatility and ease of use inspired the present invention.

SUMMARY

An insect bait device includes a cover with a plurality of scent passageways. The insect bait device further includes a bait vessel coupled to the cover by an attachment member. The insect bait device further includes a mount device having a pair of resilient hooks extending from a lower region of the bait vessel.

BRIEF DESCRIPTION OF DRAWINGS

In the following, the present invention is described in more detail with references to the drawings in which.

DETAILED DESCRIPTION OF THE EMBODIMENTS

Figure 1:
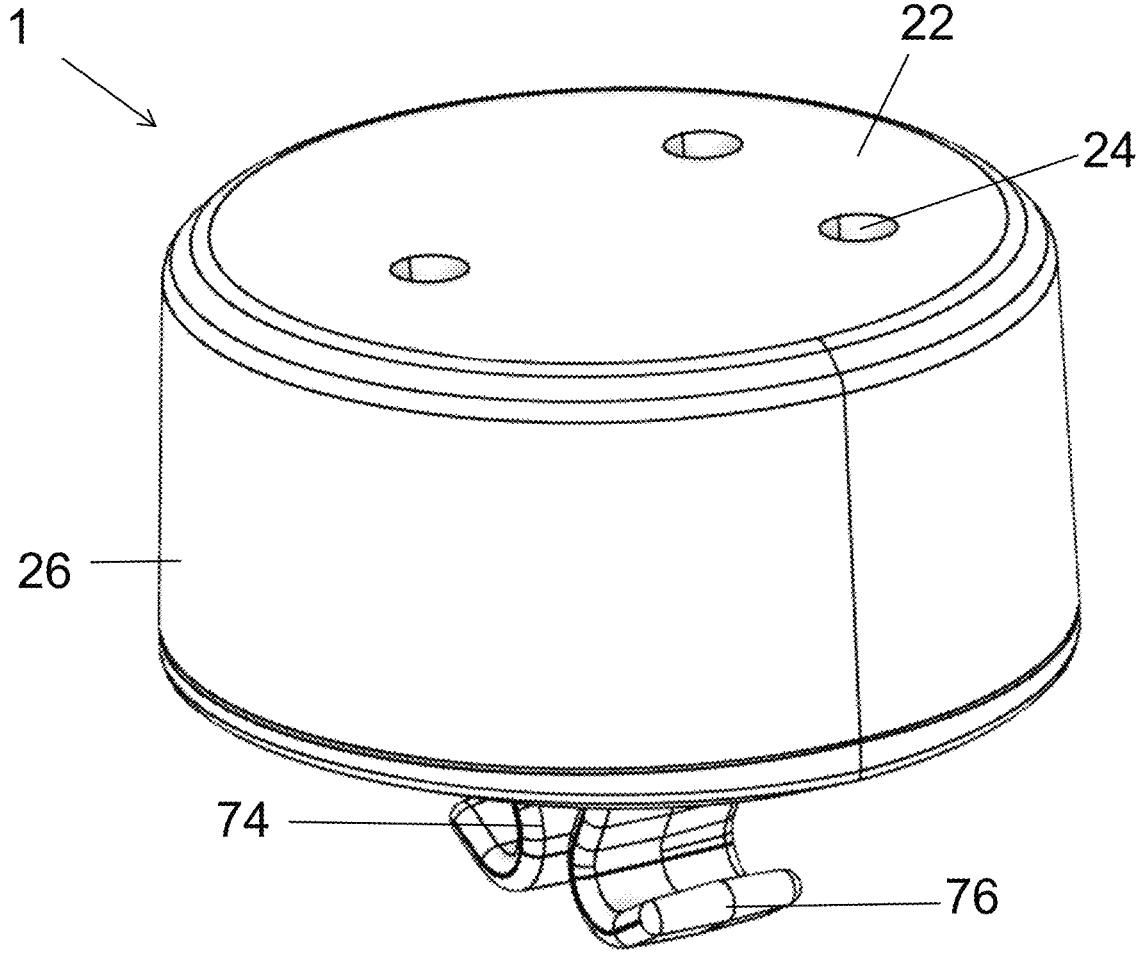
FIG. 1 illustrates an exemplary embodiment of the invention.
Figures 2, 3, 4:
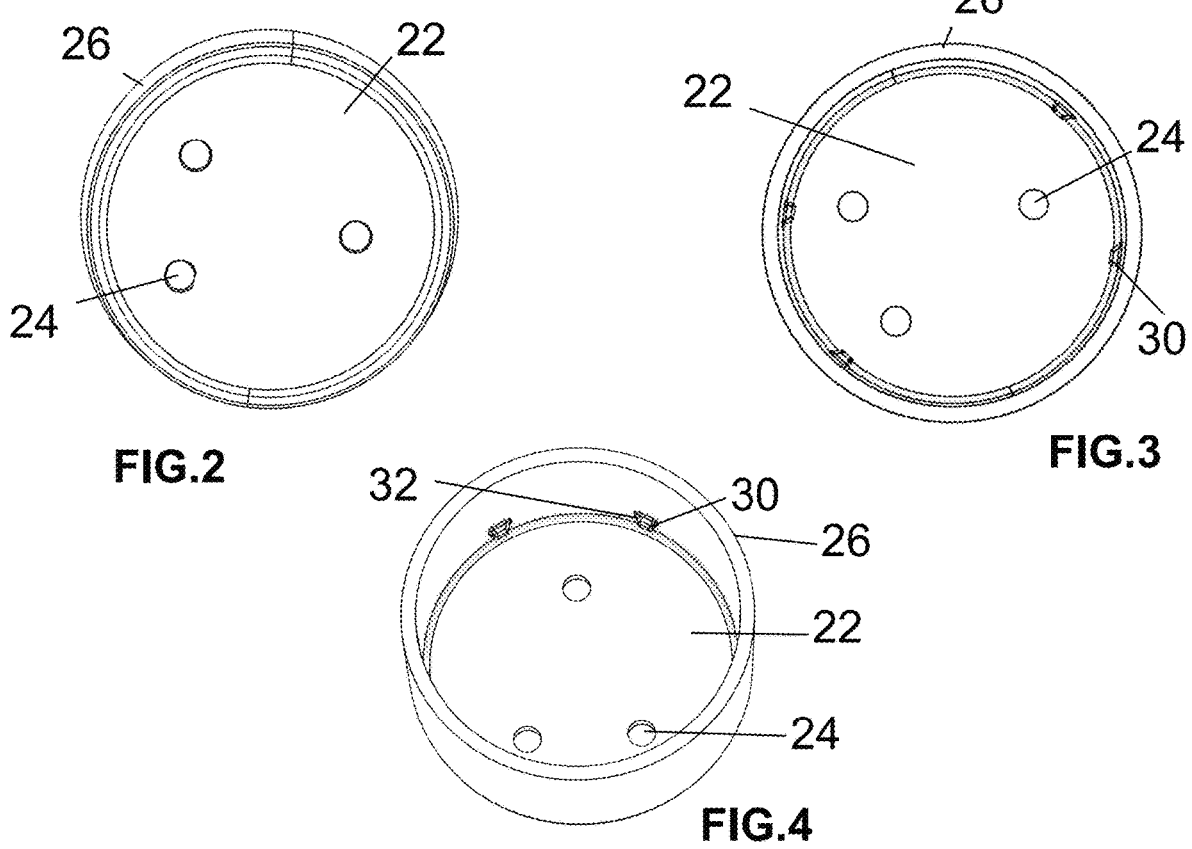
FIG. 2 illustrates a top view of the cover.
FIG. 3 illustrates a bottom view of the cover of FIG. 2.
FIG. 4 illustrates a bottom, rear view of FIG. 3.

With reference to the Figures, an insect base device 1 according to the invention is shown. In an exemplary embodiment shown, an insect base device 1 according to the invention generally includes a cover 20 and a bait vessel 40.

With reference to FIGS. 2-5, an exemplary embodiment of the cover 20 is shown and generally includes a top wall 22, at least one scent passageway 24, a side wall 26 and a plurality of projections 30.

In an exemplary embodiment, the cover 20 further includes a top wall 22. In the shown embodiment, the top wall 22 is a circular planar member. One skilled in the art would understand other polygonal designs of the top wall 22 can be implemented and is not restricted to the circular design.

In an exemplary embodiment of the invention, the cover 20 includes three scent passageways 24 that are circular in nature. One skilled in the art would understand the number and other polygonal designs of the passageway 24 can be implemented and is not restricted to only circular shaped passageways. Each scent passageway 24 is positioned on a surface of the top wall 22 and extends completely therethrough.

Figures 5, 6:
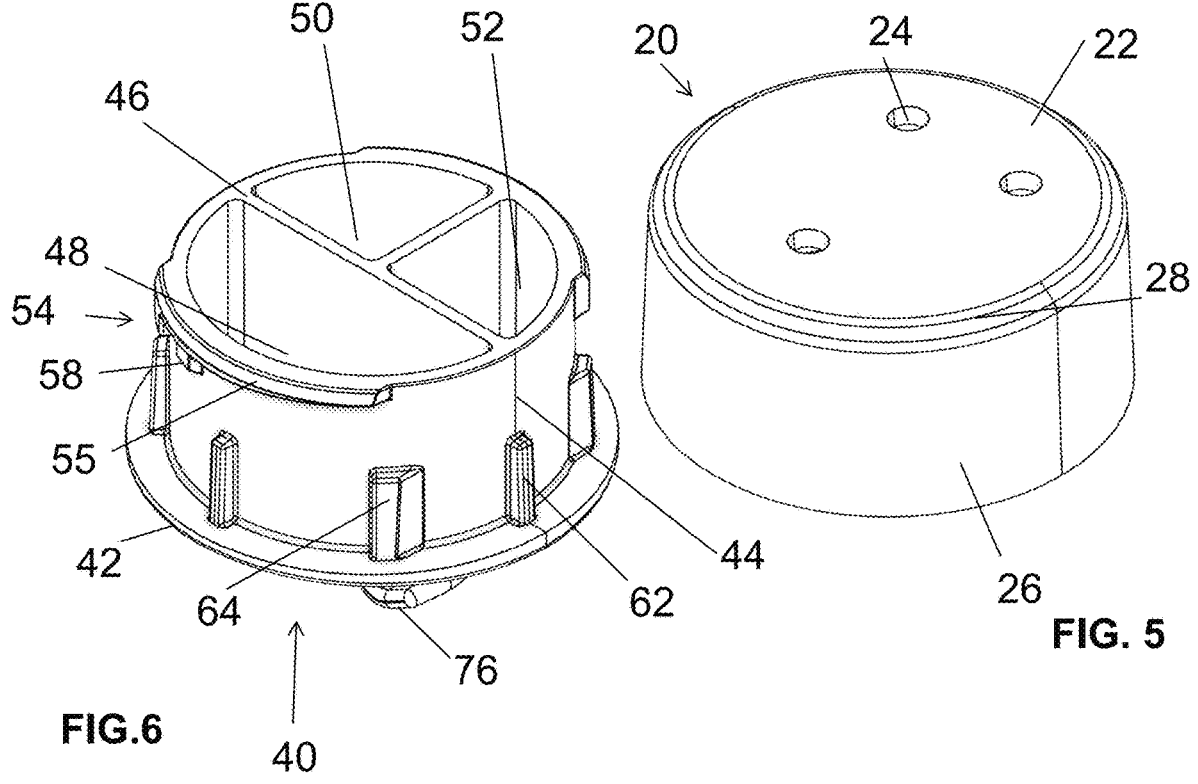
FIG. 5 illustrates a front, top, left side perspective view of the cover of FIG. 4.
FIG. 6 illustrates a front, top left side perspective view of the bait vessel.

As shown in FIGS. 2-5, side wall 26 is a planar member. In another embodiment, the side wall 26 is a pair of planar members coupled together. In particular, the side wall 26 is cylindrical and extends around the perimeter of the top wall 22 as shown. The side wall 26 joins the top wall 22 at an edge 28 as shown in FIG. 5. The edge 28 extends a distance around the perimeter of the top wall 22 to join the top wall 22 to the side wall 26. The coupling of the top wall 22 to the side wall 26 forms a curvature. One skilled in the art would understand the present curvature is not the only representation and other representations of the curvature can be utilized.

In an exemplary embodiment, the cover 20 further includes a plurality of projections 30. Each projection 30 is a protrusion positioned in a different area of an inner portion of the side wall 26. One skilled in the art would understand the positioning of each projection 30 is spaced apart accordingly and variations of the projection 30 positioning can be utilized. Each projection 30 includes further a tapering portion 32.

With reference to FIGS. 6-10, the bait vessel 40 generally includes a lower wall 42, a side wall 44, a plurality of partition walls 46, a pair of attachment members 54, a stabilizing mechanism 58, a plurality of protrusions 62, a plurality of tapered protrusions 64 and a mounting device 70.

As shown in FIG. 6, the bait vessel 40 includes the lower wall 42. The lower wall 42 includes a first side. The first side is a circular planar disk convexed outwardly. A second side of the lower wall 42 is conical and facing away from the first side. One skilled in the art would understand other polygonal shapes can be implemented to formulate the lower wall 42 and the applicant's design is not the exclusive embodiment.

The bait vessel 40 further includes the side wall 44. The side wall 44 is a cylindrical member. The side wall 44 extends upwards from the lower wall 42 and extends the distance of the lower wall 42. The side wall 44 has an overall circumference less than a circumference of the lower wall 42 as shown in FIG. 6.

The bait vessel 40 further includes the plurality of partition walls 46. The at least three partition walls 46 extend between an inner portion of the side wall 44.

The plurality of partition walls 46 include a first bait holding section 48. The first bait holding section 48 is a bifurcation of the plurality of partition walls 46. The first bait holding section 48 is a container. One skilled in the art would understand the crescent shape of the first bait holding section 48 is not the exclusive shape of the claimed invention.

The plurality of partition walls 46 further include a second bait holding section 50. The second bait holding section 50 is a further bifurcation of the first bait holding section 48 as shown. The second bait holding section 50 is a container. One skilled in the art would understand the triangular shape of the second bait holding section 50 is not the exclusive shape of the claimed invention.

The third bait holding section 52 is a mirror of the second bait holding section 50 as shown. The third bait holding section 52 is a container. One skilled in the art would understand the triangular shape of the third bait holding section 52 is not the exclusive shape of the claimed invention.

In an exemplary embodiment, the second bait holding section 50 and the third bait holding section 52 equal an area of the first bait holding section 48. One skilled in the art would understand the area of the bait holding sections may change and the current design is not the exclusive embodiment.

The bait vessel 40 further includes a pair of attachment members 54 for coupling the bait vessel 40 to the cover 20. Each attachment member 54 is a protruding portion extending around a portion of an edge of the side wall 44. Each attachment member 54 includes a gap formed between the pair of attachment members 54.

As shown in FIG. 6, the attachment member 54 further includes a rail member 55 which protrudes diagonally from the side wall 44. The rail member 55 extends over the side wall 44 forming a ledge. One skilled in the art would understand the shape of the rail member is not the exclusive embodiment.

The attachment member 54 further includes a lock mechanism 56. The lock mechanism 56 is a polygonal member coupled to the rail member 55. The lock mechanism 56 extends lower than the rail member 55 as shown in FIG. 8.

Figures 7, 8:
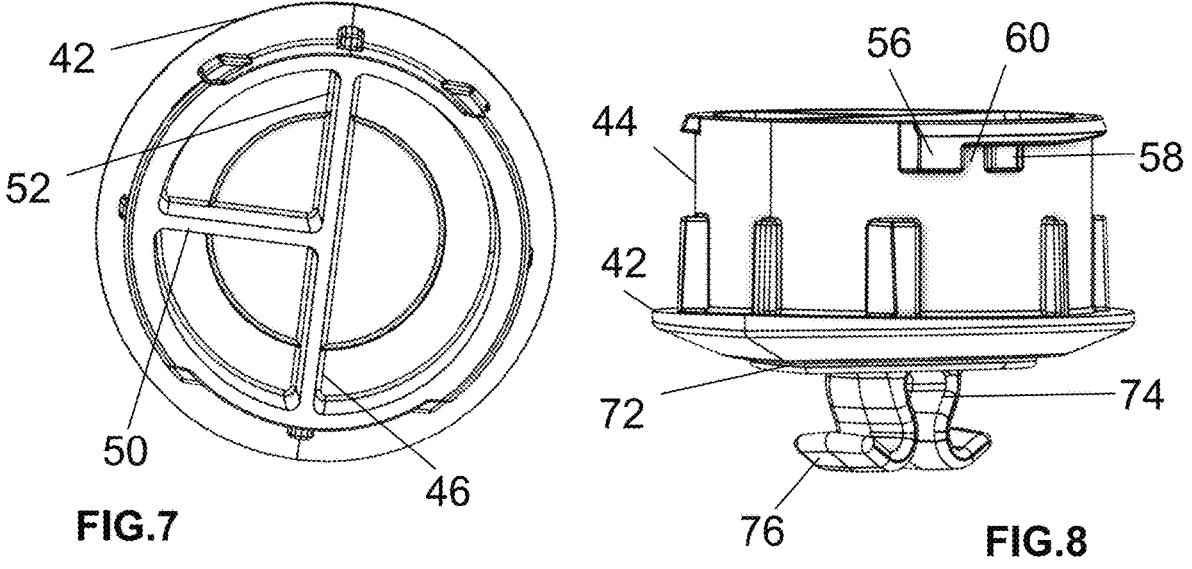
FIG. 7 illustrates a top view of FIG. 6.
FIG. 8 illustrates a side view of FIG. 7.

As shown in FIG. 8, the bait vessel 40 further includes a stabilizing mechanism 58. The stabilizing mechanism 58 is a raised member positioned adjacent the lock mechanism 56. The stabilizing mechanism 58 is positioned below the rail member 55. The stabilizing mechanism 58 further includes a tapered portion 59.

The lock mechanism 56 and the stabilizing mechanism 58 form a gap 60 as shown. One skilled in the art would understand an area of the gap 60 is not the exclusive embodiment as other variations of the area provided by the gap can be utilized.

The bait vessel 40 further includes a plurality of protrusions 62. The at least two protrusions 62 are elongated and rectangular members. Each protrusion 62 extends from the lower wall 42. One familiar with the art would understand the design of the protrusion is not the exclusive embodiment. Simultaneously, each protrusion 62 extends along a portion of the side wall 44.

The bait vessel 40 further includes a plurality of tapered protrusions 64. The at least two tapered protrusions 64 extend outward and parallel to the protrusions 62. As shown in FIGS. 6-8, the tapered protrusions are positioned between each of the protrusions 62. One skilled in the art would understand the applicant's design is not the exclusive embodiment.

Figures 9, 10:
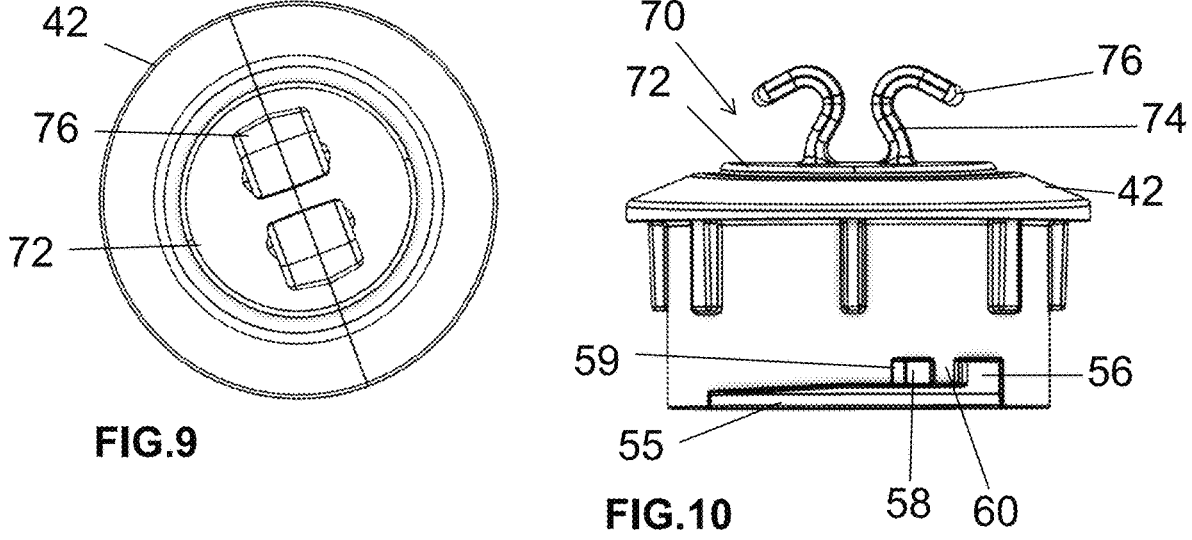
FIG. 9 illustrates a bottom view of the bait vessel and the mount device of FIG. 8.
FIG. 10 illustrates another side view of FIG. 9.
Figure 11:
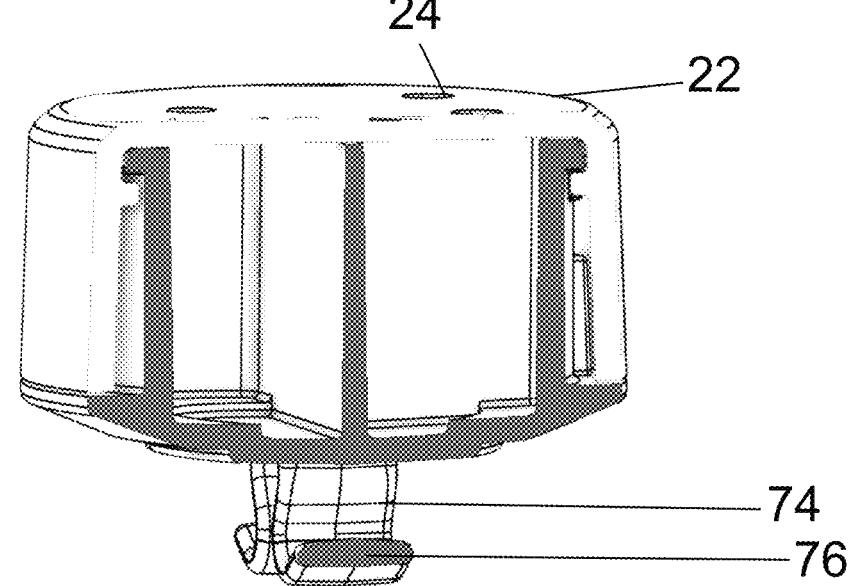
FIG. 11 illustrates a cross sectional view.

With reference to FIGS. 9-10, a mount device 70 includes a rotating base 72. The rotating base 72 is a planar member, specifically a circular disk. The rotating base 72 is extended and positioned against the second side of the lower wall 42. One skilled in the art would understand the circular shape of the rotating base 72 is not the exclusive design and other designs may be implemented.

As shown in FIGS. 8-10, the mount device 70 further includes a pair of resilient hooks 74. The at least two resilient hooks 74 are two portions of plastic that protrude outwards from the rotating base 72. Each resilient hook 74 is comprised of a relatively thin wall, allowing each of the resilient hooks 74 to flex form and attach to areas of different sizes.

In an exemplary embodiment, the resilient hooks 74 further include a protrusion 76. The protrusion 76 is a curved end member positioned at an opposing side of the resilient hook 74. Each protrusion 76 is shaped in such a way that it creates a narrow passageway between each of the protrusions 76. One skilled in the art would understand the shape of the protrusion 76 is not the exclusive embodiment and other formations can be implemented. The passageway is sized to be able to clip onto an edge of the lids of traps, as well as onto the fan grates of certain traps.

The protrusions 76 also curve away from each other and back towards the bait vessel 40. The protrusions 76 create a modified "T" shape. One skilled in the art would understand the "T" shape formation is not the exclusive embodiment as a user may flex the resilient hooks 74 to a desired shape for positioning purposes.

As assembled, the plurality of partition walls 46 include the first bait holding section 48, the second bait holding section 50 and the third bait holding section 52. Each of the bait holding sections 48, 50, 52 are mutually isolated spaces. Three volatile different substances respectively placed in the three bait holding sections 48, 50, 52: lactic acid, octene alcohol and the carbon dioxide compound which are capable of cracking and releasing ammonia gas. The three substances are volatilized outward through the plurality of scent passageways 24 of the cover 20 and constitute an odor bait forming an attraction for unwanted vermin or pests.

Among the three substances, ammonium hydrogencarbonate is a solid powder which is slowly decomposed into ammonia gas, carbon dioxide and water at room temperature. The ammonium hydrogencarbonate used in the present invention uses calcium carbonate as a binder and is extruded into a cake to reduce the volatile surface area and control the volatilization rate. The lactic acid and octenol used in the present invention are liquids which are immersed in a liquid-adsorbable carrier to reduce the fluidity thereof without affecting the volatilization rate thereof. The carrier capable of adsorbing the liquid may be a material having micropores such as non-woven fabric, sponge, or cotton wool.

The cover 20 and the bait vessel 40 are made of a plastic material. The bait vessel 40 may be sealed by a tin foil paper (not shown). The cover 20 is positioned over the bait vessel 40. The bait vessel 40 is then positioned in the cover 20. The sidewall 44 abuts against the top wall 22 of the cover 20.

The cover 20 is then rotated, the plurality of projections 30 contact the rail member 55 and continue to glide along the rail member 55 until reaching the gap 60. The projection 30 becomes immovable between the lock mechanism 56 and the stabilizing mechanism 58. Furthermore, sealing the three bait holding sections 48, 50, 52 in the bait vessel 40, and preventing the volatilization of the three substances by sealing the foil paper.

The operator will position the resilient hooks 74 through a gap in the material of the desired location. The operator will then rotate the insect base device 1 ninety degrees by the rotating base 72, locking the insect base device 1 and preventing the removal of the insect base device 1 until the base 72 is again rotated ninety degrees to release the insect base device 1.

When the operator is ready to use the attractants, the tin foil is pierced through the plurality of scent passageways 24 by a sharp object such as a needle or a thorn, and the three substances are volatized outward through the plurality of scent passageways 24.

The above description is only for the specific embodiment of the present invention and is not intended to limit the scope of the present invention. The equivalent changes or modifications made by the structures, features and principles of the present invention should be included in Within the scope of the patent application of the present invention.

What is claimed is:

1. An insect base device comprising:

a cover with a plurality of scent passageways;

a bait vessel coupled to the cover by an attachment member;

a mount device having a base and a pair of resilient hooks extending from the base, the base is positioned against a lower wall of the bait vessel and is rotatable, the pair of resilient hooks each have a protrusion that is a curved end member at an end opposite the bait vessel, the ends of the resilient hooks opposite the bait vessel are spaced apart from one another and the curved end members of the resilient hooks extend in opposite directions from one another, the base is locked by rotating the base ninety degrees and unlocked by rotating the base another ninety degrees.

2. The insect base device of claim 1, wherein the cover includes a top wall.

3. The insect base device of claim 2, wherein the plurality of scent passageways are positioned on the top wall.

4. The insect base device of claim 3, wherein the cover includes a side wall.

5. The insect base device of claim 4, wherein the cover further includes a plurality of projections positioned on the side wall.

6. The insect base device of claim 5, wherein the bait vessel includes a side wall.

7. The insect base device of claim 6, wherein the bait vessel includes a plurality of partition walls within the bait vessel.

8. The insect base device of claim 7, wherein the plurality of partition walls includes at least one bait holding section.

9. The insect base device of claim 8, wherein the attachment member further includes a lock mechanism formed at one end of the attachment member.

10. The insect base device of claim 9, wherein the attachment member further includes a stabilizing member.

11. The insect base device of claim 10, wherein the lock mechanism and the stabilizing member form a gap.

12. The insect base device of claim 11, wherein the bait vessel further includes a plurality of protrusions.

13. The insect base device of claim 1, wherein the pair of resilient hooks create a modified "T" shape structure.

* * * * *